US011219707B1

(12) United States Patent
Jacobzon et al.

(10) Patent No.: US 11,219,707 B1
(45) Date of Patent: Jan. 11, 2022

(54) IMPLANTABLE RENAL REPLACEMENT THERAPY DEVICE

(71) Applicants: Yaniv Ben-Haim, Kfar Mordechai (IL); SHAARE ZEDEK SCIENTIFIC LTD, Jerusalem (IL)

(72) Inventors: Ehud Jacobzon, Ness Zionna (IL); Yaniv Ben-Haim, Kfar Mordechai (IL)

(73) Assignee: SHAARE ZEDEK SCIENTIFIC LTD, Jerusalem (IL)

( * ) Notice: Subject to any disclaimer, the term of this patent is extended or adjusted under 35 U.S.C. 154(b) by 0 days.

(21) Appl. No.: 17/242,464

(22) Filed: Apr. 28, 2021

(51) Int. Cl.
| | |
|---|---|
| *A61M 1/16* | (2006.01) |
| *A61M 25/10* | (2013.01) |
| *A61M 1/26* | (2006.01) |
| *A61M 60/237* | (2021.01) |
| *A61M 60/122* | (2021.01) |

(Continued)

(52) U.S. Cl.
CPC ............ *A61M 1/1678* (2013.01); *A61M 1/16* (2013.01); *A61M 1/1623* (2014.02); *A61M 1/262* (2014.02); *A61M 1/267* (2014.02); *A61M 1/34* (2013.01); *A61M 1/3482* (2014.02); *A61M 25/1011* (2013.01); *A61M 60/122* (2021.01); *A61M 60/232* (2021.01); *A61M 60/237* (2021.01); *A61M 2025/1052* (2013.01); *A61M 2210/1085* (2013.01)

(58) Field of Classification Search
CPC .... A61M 1/1678; A61M 1/27; A61M 27/002; A61M 1/262; A61M 25/1011; A61M 1/1623; A61M 60/122; A61M 2210/1085; A61M 1/3482; A61M 1/34; A61M 2025/1052; A61M 60/232; A61M 60/237

See application file for complete search history.

(56) References Cited

U.S. PATENT DOCUMENTS 5,092,886 A * 3/1992 Dobos-Hardy ......... A61F 2/022
   623/23.65
5,397,354 A * 3/1995 Wilk ...................... A61F 2/022
   604/28

(Continued)

OTHER PUBLICATIONS

Clark Kensinger, MD, Seth Karp, MD, Rishi Kant, PhD†, William H. Fissell, MD et. al.; First Implantation of Silicon Nanopore Membrane Hemofilters; ASAIO J. 2016; 62(4): 491-495. doi:10.1097/MAT.0000000000000367.

Tejal A. Desai, Derek J. Hansford, Lawrence Kolinsky, Mauro Ferrari et.al.; Nanopore Technology for Biomedical Applications; Biomedical Microdevices 2:1, 11 ±40, 1999.

(Continued)

*Primary Examiner* — Leslie R Deak
(74) *Attorney, Agent, or Firm* — Pearl Cohen Zedek Latzer Baratz LLP (57) ABSTRACT

An implantable renal replacement therapy device may include: a first catheter configured to be inserted into a blood vessel in a subject's body; a pump in fluid communication with the first catheter, the pump is configured to pump subject's blood from the blood vessel; a filter in fluid communication with the pump, the filter is configured to: receive the subject's blood from the pump, and filter the received blood to provide a filtered blood and a filtrate liquid, wherein the filter is in fluid communication with the first catheter to cause an outflow of the filtered blood from the filter to the blood vessel; and a second catheter in fluid communication with the filter and configured to be inserted into an urinary bladder in the subject's body to cause an outflow of the filtrate liquid from the filter to the urinary bladder.

19 Claims, 7 Drawing Sheets

(51) Int. Cl.
*A61M 60/232* (2021.01)
*A61M 1/34* (2006.01)

(56) References Cited

U.S. PATENT DOCUMENTS

| | | | | |
|---|---|---|---|---|
| 6,022,333 | A * | 2/2000 | Kensey | A61M 1/1678 604/29 |
| 8,114,044 | B2 * | 2/2012 | Cull | A61M 1/3661 604/9 |
| 8,241,239 | B2 * | 8/2012 | Solomon | B01D 61/145 604/6.09 |
| 10,398,824 | B2 * | 9/2019 | Burnett | A61M 1/1668 |
| 2009/0318844 | A1 * | 12/2009 | Burnett | A61M 31/00 604/9 |
| 2012/0209164 | A1 * | 8/2012 | Kagan | A61B 17/0482 604/8 |
| 2015/0258268 | A1 * | 9/2015 | Collier | A61M 1/1633 210/638 |

OTHER PUBLICATIONS

William H. Fissell, Anna Dubnisheva, Abigail N. Eldridge, Shuvo Roy et. al. ; High-Performance Silicon Nanopore Hemofiltration Membranes.;J Memb Sci. Jan. 5, 2009; 326(1): 58-63. doi:10.1016/j.memsci.2008.09.039.

Dharmesh M. Kanani, William H. Fissell, Andrew L. Zydney et. al.; Permeability—Selectivity Analysis for Ultrafiltration: Effect of Pore Geometry.; J Memb Sci. Mar. 1, 2010; 349(1-2): 405. doi:10.1016/j.memsci.2009.12.003.

Steven Kim, Benjamin Feinberg, Rishi Kant, Shuvo Roy et al.; Diffusive Silicon Nanopore Membranes for Hemodialysis Applications.; Jul. 20, 2016. PLOS ONE | DOI:10.1371.

* cited by examiner

IMPLANTABLE RENAL REPLACEMENT THERAPY DEVICE

FIELD OF THE INVENTION

The present invention relates to the field of renal replacement therapy devices, and more particularly, to fully implantable renal replacement therapy devices.

BACKGROUND OF THE INVENTION

Subjects suffering from end-stage renal diseases are typically required to undergo at least one of hemodialysis, peritoneal dialysis or continuous renal replacement therapy treatments while waiting for kidney transplantation. However, these treatments may cause significant inconvenience to a subject. For example, subjects undergoing hemodialysis treatment are required to attend a treatment facility at least three times a week for several hours each time.

SUMMARY OF THE INVENTION

Some embodiments of the present invention may provide an implantable renal replacement therapy device, the device may include: a first catheter configured to be inserted into a blood vessel in a subject's body; a pump in fluid communication with the first catheter, the pump is configured to pump subject's blood from the blood vessel; a filter in fluid communication with the pump, the filter is configured to: receive the subject's blood from the pump, and filter the received blood to provide a filtered blood and a filtrate liquid, wherein the filter is in fluid communication with the first catheter to cause an outflow of the filtered blood from the filter to the blood vessel; and a second catheter in fluid communication with the filter and configured to be inserted into an urinary bladder in the subject's body to cause an outflow of the filtrate liquid from the filter to the urinary bladder.

In some embodiments, the first catheter may include: a first lumen in fluid communication with the pump; and a second lumen in fluid communication with the filter.

In some embodiments, the first catheter may include a first catheter connector configured to connect the first catheter to the blood vessel and to prevent motion of the first catheter with respect to the blood vessel.

In some embodiments, the first catheter connector may include: a first inflatable member connected to an outer surface of the first catheter; and a second inflatable member connected to the outer surface of the first catheter at a predefined first distance from the first inflatable member and a predefined second distance from a distal sharp end of the first catheter; wherein, when inflated, the first and second inflatable members are configured to receive a wall of the blood vessel therebetween to prevent motion of the first catheter with respect to the blood vessel.

In some embodiments, the pump is an axial or centrifugal flow pump.

In some embodiments, the filter has a substantially flat flexible structure.

In some embodiments, the filter has a substantially flat and thin flexible structure, having a uniform thickness substantially smaller than a width or length of the filter.

In some embodiments, the filter may include: a filtrate collecting bag in fluid communication with the second catheter; and a filtering membrane positioned within the filtrate collecting bag, the filtering membrane having filtering membrane interior in fluid communication with the pump and configured to receive the subject's blood from the pump.

In some embodiments, the filtering membrane may be made of a silicone and may include a plurality of pores having high permeability for selected liquids and selected electrolytes.

In some embodiments, the filtering membrane has a wavy structure in its cross-section.

In some embodiments, the filter may further include a second membrane surrounding the filtering membrane, the second membrane having lower permeability for the selected liquids and the selected electrolytes as compared to the permeability of the filtering membrane to cause reabsorption of excess liquids of the selected liquids and excess electrolytes of the selected electrolytes within the filtered blood.

In some embodiments, the filter may include a conduit for injection of liquids into the filter, wherein the conduit is configured to extend external to the subject's body.

In some embodiments, the second catheter may include an adjustable ring configured to adjust a diameter of the second catheter based on a desired blood filtration rate and a desired filtrate outflow rate.

In some embodiments, the second catheter may include a second catheter connector configured to connect the second catheter to the urinary bladder and to prevent motion of the second catheter with respect to the urinary bladder.

In some embodiments, the second catheter connector may include: a first inflatable member connected to an outer surface of the second catheter; and a second inflatable member connected to the outer surface of the second catheter at a predefined first distance from the first inflatable member and a predefined second distance from a distal sharp end of the second catheter; wherein, when inflated, the first and second inflatable members are configured to receive a wall of the urinary bladder therebetween to prevent motion of the second catheter with respect to the urinary bladder.

In some embodiments, the device may include a power source configured to be implanted in the subject's body to provide power to the pump.

In some embodiments, the power source is chargeable.

In some embodiments, the power source is wirelessly chargeable.

In some embodiments, the device may further include an external non-implantable power source to at least one of: (i) provide power to the pump, and (ii) charge a power source that provides power to the pump.

In some embodiments, the device may further include one or more sensors configured to be implanted in the subject's body and measure one or more properties of at least one of the subject's blood and subject's blood filtration work products.

In some embodiments, the device may further include a controller configured to: receive the one or more measured properties from the one or more sensors; and control a pump rate or speed of the pump based on the one or more measured properties and a desired filtration rate of the subject's blood.

In some embodiments, the controller is configured to generate one or more notifications based on the one or more measured properties.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Figure 1A:
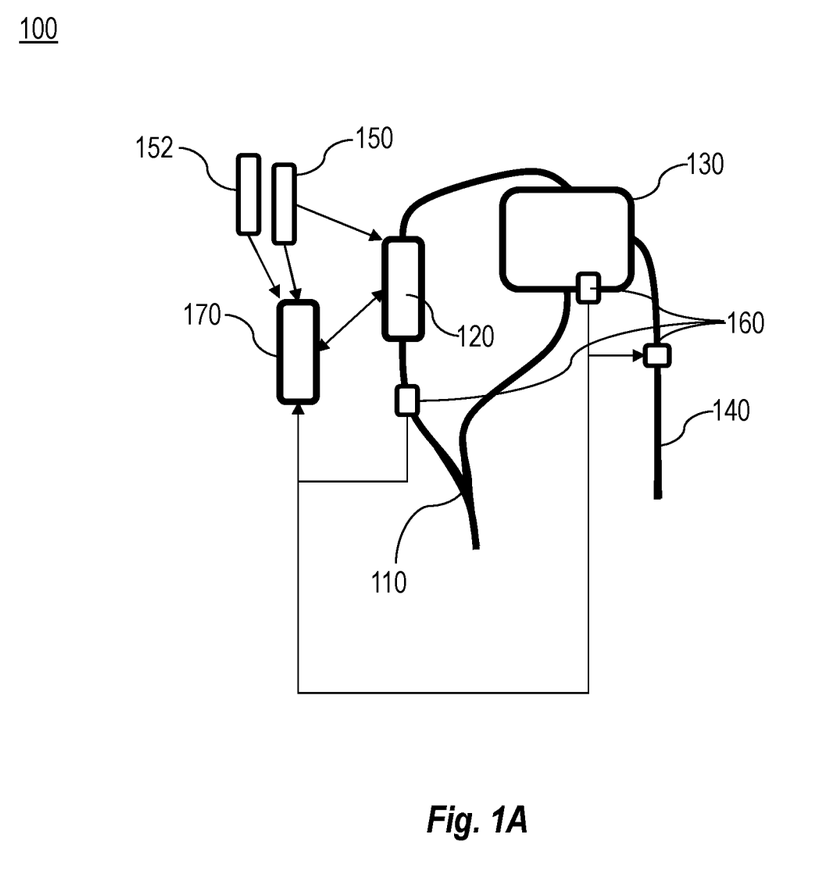
FIG. 1A is a schematic illustration of an implantable renal replacement therapy device, according to some embodiments of the invention.

Reference is now made to FIG. 1A, which is a schematic illustration of an implantable renal replacement therapy device 100, according to some embodiments of the invention.

Figure 1B:
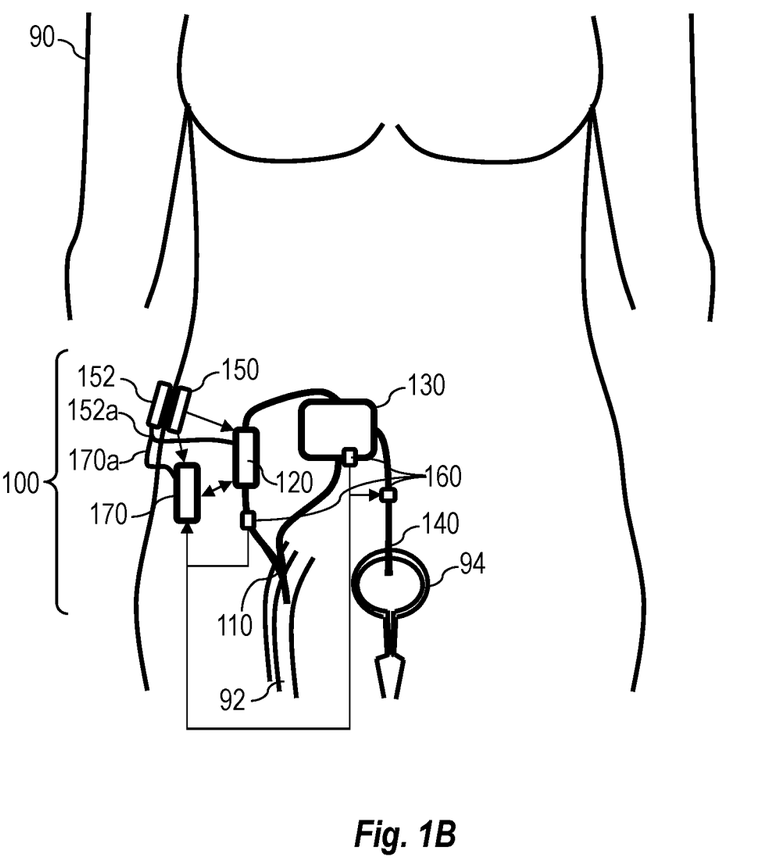
FIGS. 1B and 1C are schematic illustrations of an implantable renal replacement therapy device, implanted in a subject's body, according to some embodiments of the invention.
Figure 1C:
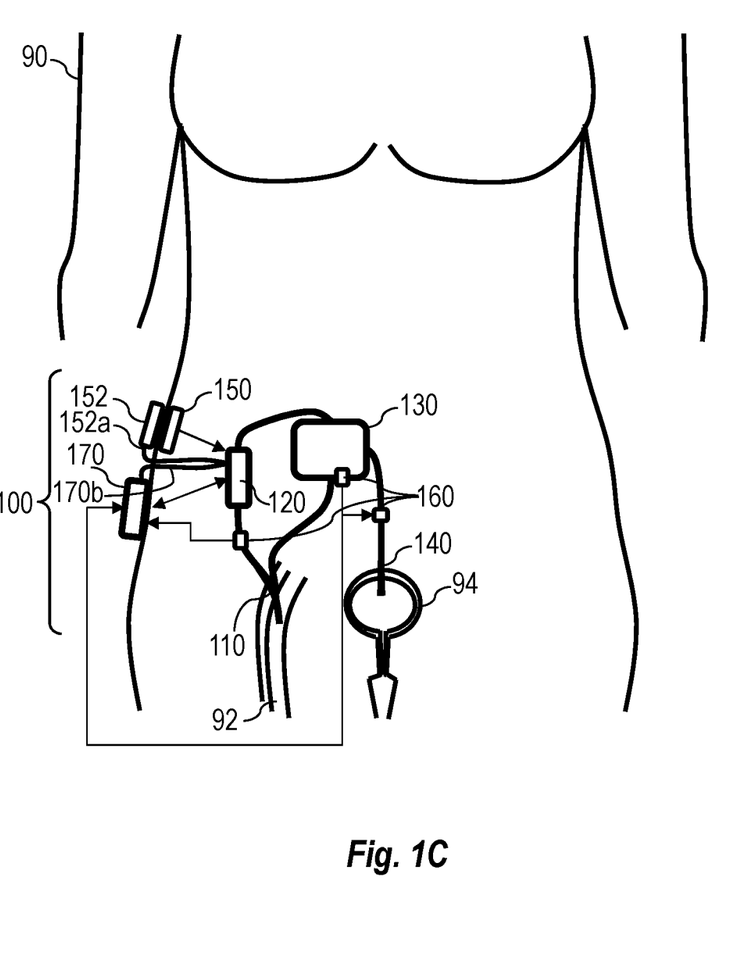

Reference is also made to FIGS. 1B and 1C, which are schematic illustrations of an implantable renal replacement therapy device 100, implanted in a subject's body 90, according to some embodiments of the invention.

According to some embodiments of the invention, device 100 may include a first catheter 110, a pump 120, a filter 130 and a second catheter 140. Device 100 may be configured to be fully implanted in subject's body 90. Device 100 may be fully implanted in subject's body 90 such that none of its components protrudes from subject's body 90. For example, device 100 may be configured to be implanted in subject's body 90 between abdominal wall muscles and a transversalis fascia.

First catheter 110 may be configured to be inserted into a blood vessel 92. In some embodiments, first catheter 110 may be a venous catheter configured to be inserted into a central vein (e.g., as schematically shown in FIGS. 1B and 1C). One embodiment of first catheter 110 is described below with respect to FIGS. 2A, 2B and 2C. However, other embodiments of first catheter 110 are possible.

Pump 120 may be in fluid communication with first catheter 110. Pump 120 may be configured to pump subject's blood from blood vessel 92. In some embodiments, pump 120 may be an axial flow pump. In some embodiments, pump 120 may be a centrifugal flow pump. In some embodiments, pump 120 may have a displacement volume of 15-25 ml (e.g., 20 ml). In some embodiments, pump 120 may have a weight of 60-100 gr (e.g., 80 gr). In some embodiments, pump 120 may include a single impeller rotatably supported within a cylindrical tube. In some embodiments, pump 120 may have a length of 4-6 cm (e.g., 5 cm). In some embodiments, pump 120 may have an outer diameter of 1-2 cm (e.g., 1.5 cm). In some embodiments, pump 120 may be configured to create high hydrostatic pressure within filter 130. Pump 120 may be configured to generate filtrate in a production rate of 30-100 ml/hour (e.g., 50 ml/hour). Pump 120 may be configured to generate blood flow of 100-300 ml/minute (e.g., 150 ml/minute).

Filter 130 may be in fluid communication with pump 120. Filter 130 may be configured to receive the subject's blood being pumped by pump 120. Filter 130 may be configured to filter the received subject's blood to provide a filtered blood and a filtrate liquid. Filter 130 may be in fluid communication with first catheter 110 to cause an outflow of the filtered blood from filter 130 to blood vessel 92. Filter 130 may be thin and flat, having a uniform thickness substantially smaller than a width or length of the filter. For example, a thickness of filter 130 may be 3 times, 5 times, or 10 times or more smaller than a width and a length of filter 130. For example, filter 130 may have a length of 10-15 cm (e.g., 12 cm), a width of 5-15 cm (e.g., 10 cm) and a thickness of 1-3 cm (e.g., 2 cm). In some embodiments, filter 130 may be made of flexible materials. One embodiment of filter 130 is described below with respect to FIGS. 3A and 3B. However, other embodiments of filter 130 are possible.

Second catheter 140 may be in fluid communication with filter 130. Second catheter 140 may be configured to be inserted into a subject's urinary bladder 94 to cause an outflow of the filtrate liquid from filter 130 to urinary bladder 94. One embodiment of second catheter 140 is described below with respect to FIGS. 4A, 4B and 4C. However, other embodiments of second catheter 140 are possible.

In some embodiments, device 100 may include a power source 150. Power source 150 may provide power to pump 120. In some embodiments, power source 150 may be configured to be implanted in subject's body 90 (e.g., as shown in FIGS. 1B and 1C). For example, power source 150 may be configured to be fully implanted in subject's body 90 (e.g., such that none of its components protrudes external to subject's body 90). In some embodiments, power source 150 may be chargeable. For example, power source 150 may be wirelessly chargeable.

In some embodiments, device 100 may include an external power source 152. In some embodiments, external power source 152 is not implantable. In some embodiments, external power source 152 may be configured to be fastened to subject's body 90 (e.g., as schematically shown in FIGS. 1B and 1C). For example, external power source 152 may include one or more fasteners configured to fasten external power source 152 to subject's body (not shown). In some embodiments, external power source 152 may be configured to provide power to pump 120. In some embodiments, external source 152 may be configured to charge power source 150. In some embodiments, external power source 152 may be connected to pump 120 using a flexible driveline 152a configured to extend external to subject's body 90 (e.g., as shown in FIGS. 1B and 1C).

In some embodiments, device 100 may include of one or more sensors 160. One or more sensors 160 may be configured to measure one or more properties of the subject's blood and/or of the subject's blood filtration work products. For example, one or more sensors 160 may measure a concentration of electrolytes in the subject's blood, a concentration of ions in the subject's blood, a filtration rate of the subject's blood, an amount of the filtered blood being produced by filter 130, an amount of the filtrated liquid being produced by filter 130, a flow rate of the subject's blood through device 100, etc. In some embodiments, one or more sensors 160 may be configured to be implanted in subject's body 90. For example, one or more sensors 160 may be configured to be fully implanted in subject's body 90 (e.g., such that none of its components protrudes external to subject's body 90). One or more sensors 160 may be positioned, for example, within and/or on first catheter 110, filter 130, second catheter 140, etc. Some examples of possible positions of one or more sensors 160 are schematically shown in FIG. 1. However, other positions of one or more second filters 160 are possible.

In some embodiments, device 100 may include a controller 170. In some embodiments, controller 170 may be configured to be implanted in subject's body 90 (e.g., as schematically shown in FIG. 1B). For example, controller 170 may be configured to be fully implanted in subject's body 90 (e.g., such that none of its components protrudes external to subject's body 90). In some embodiments, controller 170 may be connected to external power source 152 using a flexible driveline 170a configured to extend external to subject's body 90 (e.g., as schematically shown in FIG. 1B).

In some embodiments, controller 170 is not implantable. In some embodiments, controller 170 may be configured to be fastened to subject's body 90 (e.g., as schematically shown in FIG. 1C). For example, controller 170 may include one or fasteners configured to fasten controller 170 to subject's body (not shown). In some embodiments, controller 170 may be connected to pump 120 using a flexible driveline 170b configured to extend external to subject's body 90 (e.g., as shown in FIG. 1C).

Controller 170 may be in communication (e.g., wired or wireless) with one or more sensors 160. Controller 170 may receive the one or more measured properties from one or more sensors 160. In some embodiments, controller 170 may control a pump rate of pump 120 based on the one or more measured properties and a preset/desired filtration rate of the subject's blood. For example, controller 170 may implement a machine learning algorithm configured to receive as an input the one or more measured properties, output the required pump rate and control pump 120 according to the required pump rate. In some embodiments, controller 170 may generate one or more notifications based on the one or more measured properties. For example, controller 170 may generate a notification alert if at least one of the one or more measured properties is not within a predefined range. Controller 170 may transmit the one or more notifications to an external computing device. The external computing device may include at least one of a smartphone (for example belonging to the subject), a personal computer (for example of a treating healthcare professional), and a server (for example of a healthcare facility). In some embodiments, controller 170 may transmit the one or more measured properties to the external computing device for further analysis.

In some embodiments, controller 170 may monitor one or more operational parameters of device 100. For example, controller 170 may monitor the pump rate or speed of pump 120, a charging level of power source 150, etc. In some embodiments, controller 170 may generate one or more notifications based on the one or more monitored operational parameters. For example, controller 170 may generate a notification alert if the measured operational parameters indicate that the charging level of power source 150 is below a predefined charging level threshold and/or that the pump rate of pump 120 is below a predefined pump rate threshold, etc. In some embodiments, controller 170 may transmit the one or more notifications to the external computing device.

Figure 2A:
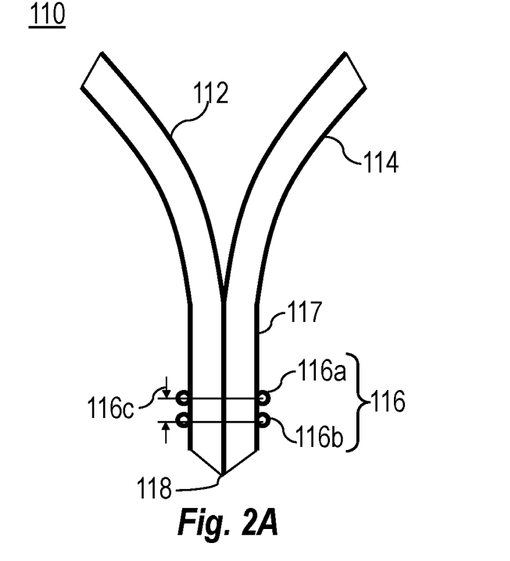
FIGS. 2A and 2B are schematic illustrations of a first catheter of an implantable renal replacement therapy device, according to some embodiments of the invention.
Figure 2B:
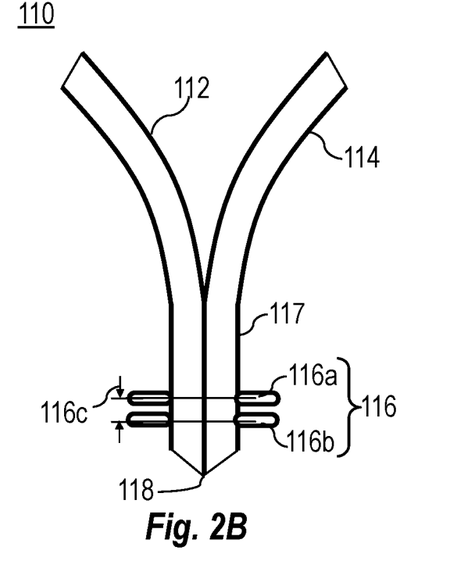

Reference is now made to FIGS. 2A and 2B, which are schematic illustrations of a first catheter 110 of an implantable renal replacement therapy device 100, according to some embodiments of the invention.

Figure 2C:
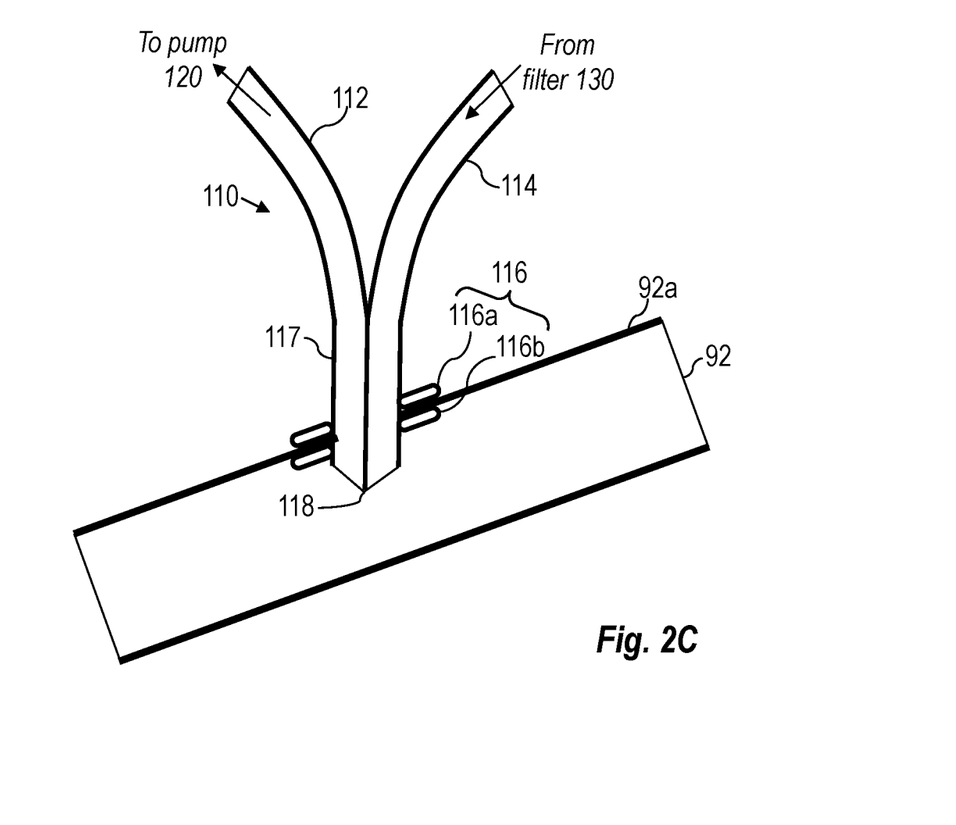
FIG. 2C is a schematic illustration of a first catheter inserted into a blood vessel, according to some embodiments of the invention.

Reference is also made to FIG. 2C, which is a schematic illustration of a first catheter 110 inserted into a blood vessel 92, according to some embodiments of the invention.

According to some embodiments of the invention, first catheter 110 may be a dual-lumen catheter and may include a first lumen 112 and a second lumen 114. First lumen 112 of first catheter 110 may be connected to pump 120. Second lumen 114 of first catheter 110 may be connected to filter 130.

In some embodiments, first catheter 110 may include a first catheter connector 116. First catheter connector 116 may be configured to connect first catheter 110 to blood vessel 92. In some embodiments, first catheter connector 116 may be configured to connect first catheter 110 to blood vessel 92 and to prevent motion of first catheter 110 with respect to blood vessel 92.

In some embodiments, first catheter connector 116 may include a first inflatable member 116a and a second inflatable member 116b. First inflatable member 116a and second inflatable member 116b may be connected to an outer surface 117 of first catheter 110 at a predefined distance 116c with respect to each other. First inflatable member 116a and second inflatable member 116b may be connected to first catheter 110 at a predefined distance from a distal sharped end 118 of first catheter 110. For example, the distance between second inflatable member 116b and distal sharp end 118 of first catheter 110 may range between 0.5-1 cm. In some embodiments, an outer diameter of first catheter 110 may range between 0.5-0.8 cm. In some embodiments, first catheter 110 may include two fluid conduits each for providing a pressurized fluid to one of first inflatable member 116a and second inflatable member 116b for inflating and deflating the respective inflatable member. When inflated, first inflatable member 116a and second inflatable member 116b may be configured to receive a wall 92a of blood vessel 92 therebetween to prevent motion of first catheter 110 with respect to blood vessel 92 (e.g., as shown in FIG. 2C).

First inflatable member 116a and second inflatable member 116b positioned adjacent to distal sharp end 118 of first catheter 110 may ensure safe and stable connection of first catheter 110 to blood vessel 92 while requiring only a short section of first catheter 110 to be inserted into blood vessel 92. Having short section of first catheter 110 within blood vessel 92 may significantly reduce catheter-associated complications in blood vessel 92 (for example, thrombosis and infection) as compared to catheters that require relatively long sections thereof to be inserted into the blood vessel.

Figure 3A:
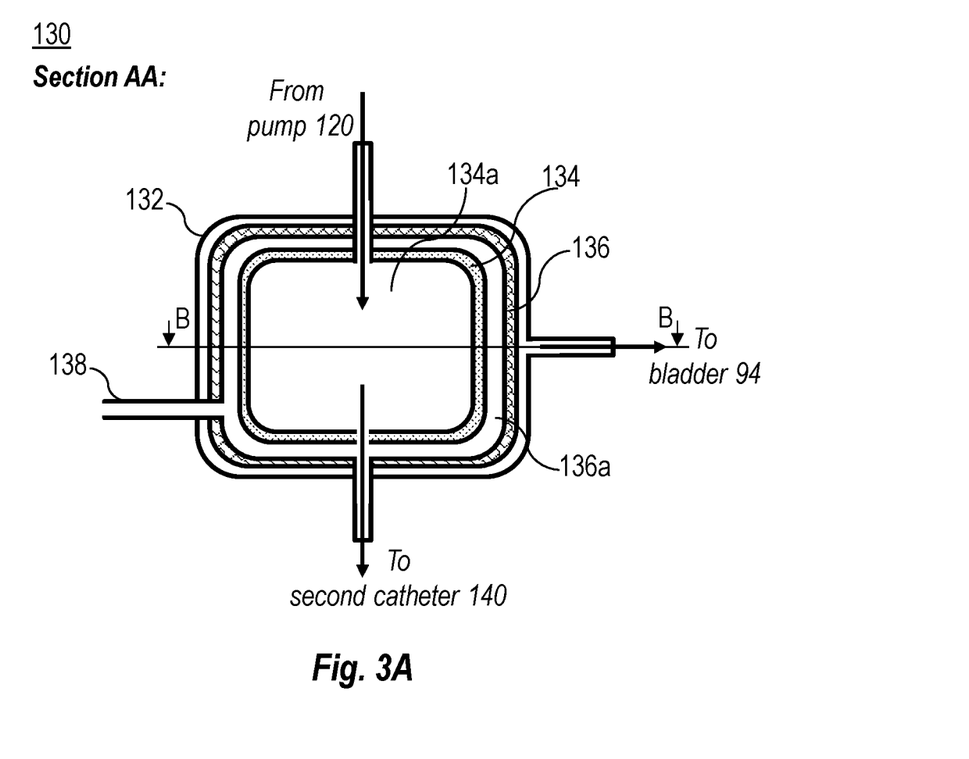
FIGS. 3A and 3B are schematic illustrations of a filter of an implantable renal replacement therapy device, according to some embodiments of the invention.
Figure 3B:
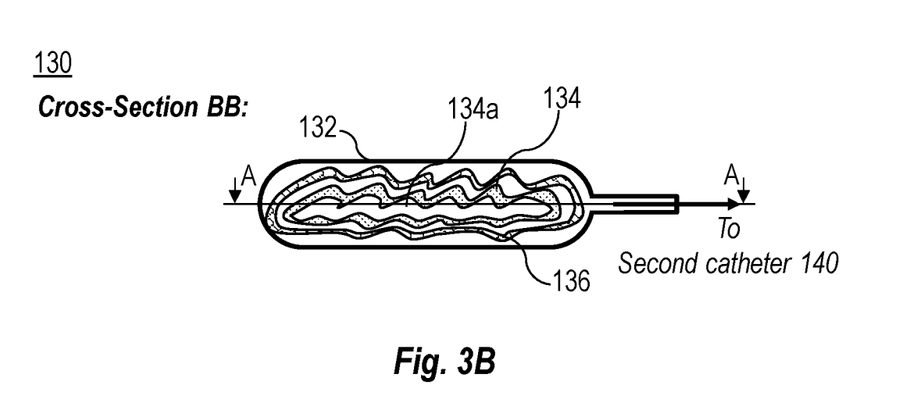

Reference is now made to FIGS. 3A and 3B, which are schematic illustrations of a filter 130 of an implantable renal replacement therapy device 100, according to some embodiments of the invention.

FIG. 3A shows a schematic sectional view AA and FIG. 3B shows a schematic cross-sectional view BB of filter 130.

According to some embodiments of the invention, filter 130 may include a filtrate liquid collecting bag 132 and a filtering membrane 134.

Filtrate liquid collecting bag 132 may receive the filtrated liquid. Filtering liquid collecting bag 132 may be in fluid communication with second catheter 140 to cause an outflow of the filtrate liquid from filtering liquid collecting bag 132 to urinary bladder 94 through second catheter 140.

Filtering membrane 134 may be positioned within filtrate liquid collecting bag 132. Filtering membrane 134 may have a filtering membrane interior 134a in fluid communication with pump 120. Filtering membrane interior 134a may be adapted to receive the subject's blood from pump 120.

In some embodiments, filtering membrane 134 may be made of a silicone. Filtering membrane 134 may include a plurality of pores having high permeability for selected liquids and selected electrolytes that need to be filtered from the subject's blood. For example, the substances that need to be filtered from the subject's blood may include urea, creatinine, potassium, hydrogen, uric acid, etc. In some embodiments, the pores in filtering membrane 134 may be nanopores. In some embodiments, the pores in filtering membrane 134 may have uniform (or substantially uniform) size. The uniform nanopores of filtering membrane 134 may, for example, reduce hydraulic resistance of filtering membrane 134 while maintaining molecular selectivity of filtering membrane 134. In some embodiments, the pores in filtering membrane 134 may have an elongated shape in the form of a slit. For example, slit-shaped nanopores of filtering membrane 134 may reduce hydraulic resistance of filtering membrane 134. In some embodiments, filtering membrane 134 may be electrically charged. In some embodiments, a surface of filtering membrane 134 may be modified using polyethylene glycol (PEG). Modification of the surface of filtering membrane 134 with PEG may, for example, reduce fouling filtering membrane 134 by globular proteins.

In some embodiments, filter 130 may include a second membrane 136. Second membrane 136 may surround filtering membrane 134. In some embodiments, second membrane 136 may have lower permeability for the selected liquids and the selected electrolytes than the filtering membrane 134. Accordingly, second membrane 136 may prevent excess liquid of the selected liquids and excess electrolyte of the selected electrolytes, which passed through filtering membrane 134, from passing through second membrane 136, thus causing reabsorption of the excess liquids and the excess electrolytes within the filtered blood. For example, the substances that need to be reabsorbed within the filtered blood may include water (e.g., up to 95% of water), and $Na^+$, $K^+$, $Ca^{2+}$, $Mg^{2+}$, $HCO^{3-}$, $Cl^-$, etc. In some embodiments, second membrane 136 may have a plurality of pores. In various embodiments, the pores of second membrane 136 may have different shape and/or size as compared to pores of filtering membrane 134. In some embodiments, second membrane 136 may be electrically charged. In some embodiments, the electrical charge of second membrane 136 may be different as compared to the electrical charge of filtering membrane 134.

In some embodiments, second membrane 136 may be covered with renal tubular cells. For example, samples of subject's omental tissue may be obtained which may be then reprogrammed to become pluripotent stem cells. The pluripotent stem cells may be then differentiated into renal tubular cells. The renal tubular cells may be processed into personalized subject-specific hydrogel which may be used together with extracellular matrix and endothelial cells to form a bio ink for three-dimensional printing of a living functioning patch of renal tubular cells. The renal tubular cells may be then used to cover second membrane 136.

In various embodiments, filtering membrane 134 and/or second membrane 136 may have a wavy structure in their respective cross-section (e.g., as schematically shown in FIG. 3B). Arranging the membranes in the wavy structure may increase a filtering surface of the membranes as compared to membranes having non-wavy structure.

A thickness of filter 130 may be significantly smaller than a width and/or a length of filter 130. For example, filter 130 may have a length of 10-15 cm (e.g., 12 cm), a width of 5-15 cm (e.g., 10 cm) and a thickness of 1-3 cm (e.g., 2 cm).

In some embodiments, filter 130 may include a conduit 138. Conduit 138 may be configured to extend external to subject's body 90. Conduit 138 may be used for direct injection of liquids and drugs into filter 130 for cleaning filter 130. For example, thrombolytic drugs may be injected into filter 130 via conduit 138 to clean blood clots from filter 130. In some embodiments, conduit 138 may be in fluid communication with a gap 136a between filtering membrane 134 and second membrane 136 of filter 130.

Figure 4A:
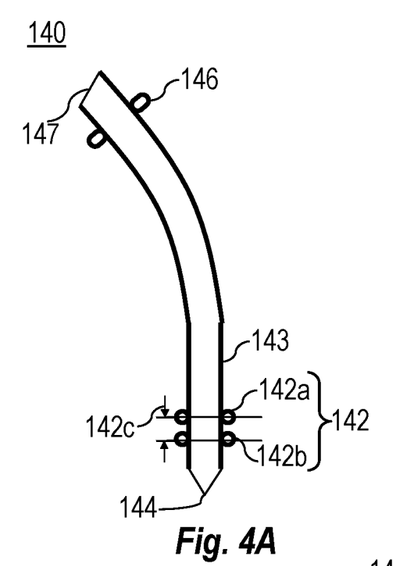
FIGS. 4A and 4B are schematic illustrations of a second catheter of an implantable renal replacement therapy device, according to some embodiments of the invention.
Figure 4B:
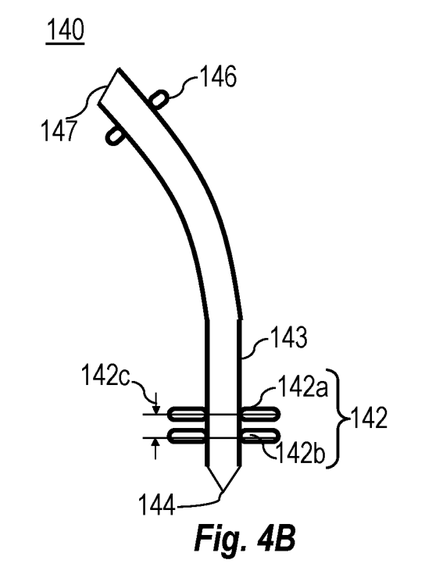

Reference is now made to FIGS. 4A and 4B, which are schematic illustrations of a second catheter 140 of an implantable renal replacement therapy device 100, according to some embodiments of the invention.

Figure 4C:
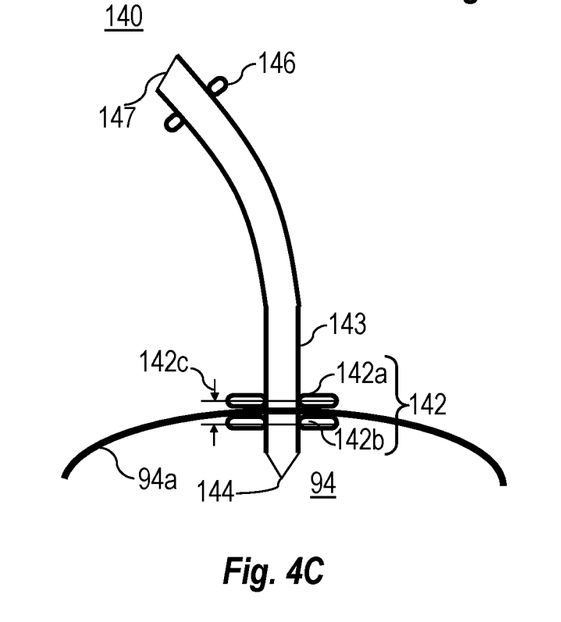
FIG. 4C is a schematic illustration of a second catheter of an implantable renal replacement therapy device, inserted into a urinary bladder, according to some embodiments of the invention.

Reference is also made to FIG. 4C, which is a schematic illustration of a second catheter 140 of an implantable renal replacement therapy device 100, inserted into an urinary bladder 94, according to some embodiments of the invention.

According to some embodiments of the invention, second catheter 140 may include a second catheter connector 142. Second catheter connector 142 may be configured to connect second catheter 140 to urinary bladder 94. In some embodiments, second catheter connector 142 may be configured to connect second catheter 140 to urinary bladder 94 and to prevent motion of second catheter 140 with respect to urinary bladder 94.

In some embodiments, second catheter connector 142 may include a first inflatable member 142a and a second inflatable member 142b. First inflatable member 142a and second inflatable member 142b may be connected to an outer surface 143 of second catheter 140 at a predefined distance 142c with respect to each other. First inflatable member 142a and second inflatable member 142b may be connected to second catheter 140 at a predefined distance from a distal sharp end 144 of second catheter 140. For example, the distance between second inflatable member 142b and distal sharp end 144 of second catheter 140 may range between 1-2 cm. In some embodiments, second catheter 140 may include two fluid conduits each for providing a pressurized fluid to one of first inflatable member 142a and second inflatable member 142b for inflating and deflating the respective inflatable member. When inflated, first inflatable member 142a and second inflatable member 142b may be configured to receive a wall 94a of urinary bladder 94 therebetween to prevent motion of second catheter 140 with respect to urinary bladder (e.g., as shown in FIG. 4C).

In some embodiments, second catheter 140 may include an adjustable ring 146 to adjust a diameter of second catheter 140. For example, adjustable ring may be connected to outer surface 143 of second catheter 140, e.g., adjacent to a proximal end 147 of second catheter 140 at which second catheter 140 is connected to filter 130. The diameter of second catheter 140 may be adjusted using adjustable ring 146, for example during and/or after implantation of device 100, based on, e.g., a desired filtration rate of the subject's blood and/or based on a desired outflow of the filtrate liquid from filter 130. In some embodiments, adjustable ring 146 may be inflatable. In some embodiments, adjustable ring 146 may include a fluid conduit for providing a pressurized fluid to adjustable ring 146 for inflating and deflating adjustable ring 146 (not shown).

Figure 5:
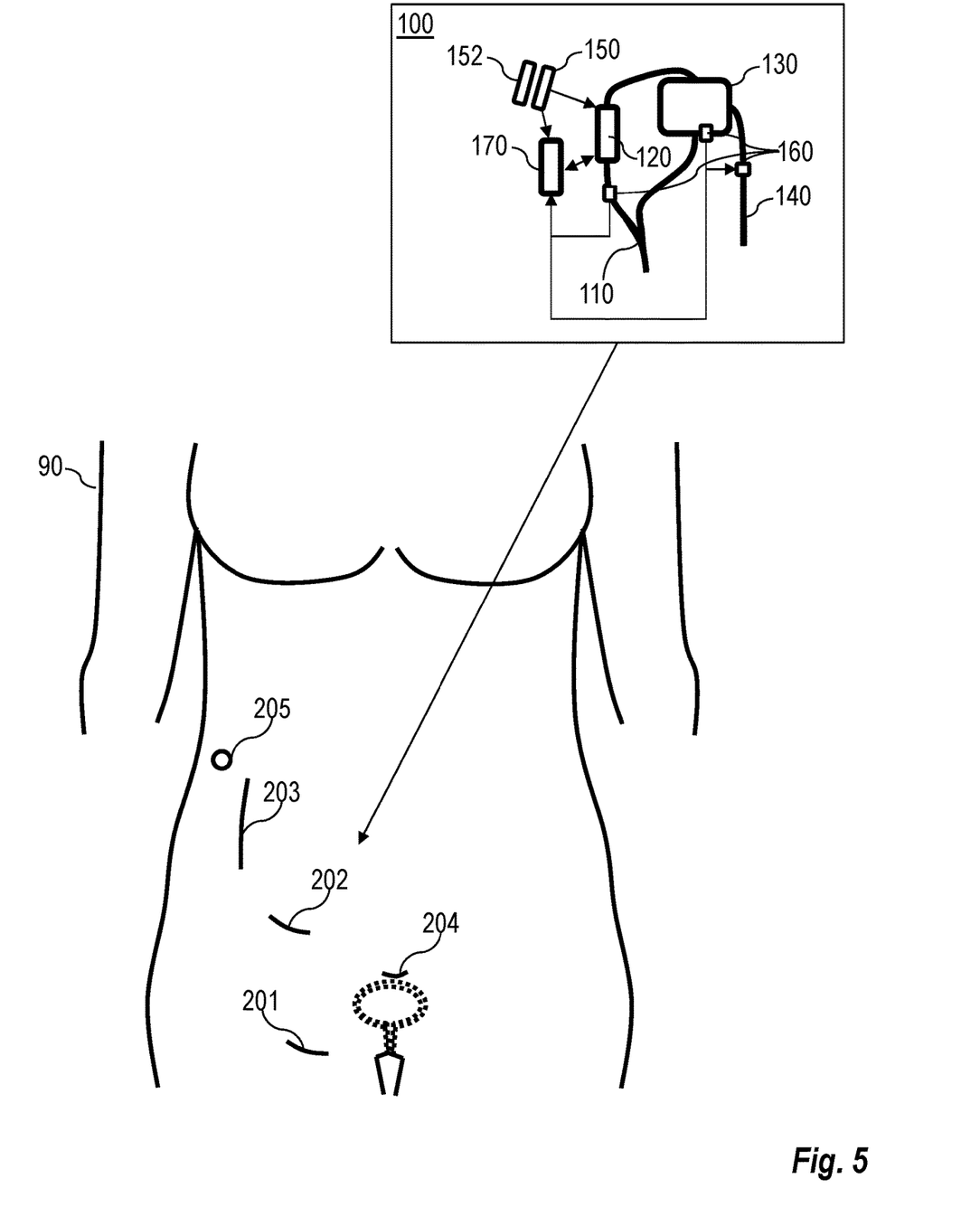
FIG. 5 is a schematic illustration of an implantable renal replacement therapy device, a subject's body and incisions to be made in the subject's body in order to implant the implantable renal replacement therapy device, according to some embodiments of the invention.

Reference is now made to FIG. 5, which is a schematic illustration of an implantable renal replacement therapy device 100, subject's body 90 and incisions 201-204 to be made in subject's body 90 in order to implant the implantable renal replacement therapy device 100, according to some embodiments of the invention.

Implantable renal replacement therapy device 100 may be fully implanted in subject's body 90 such that none of its components protrudes from subject's body 90. For example, device 100 may be implanted in subject's body 90 between abdominal wall muscles a transversalis fascia membrane. Device 100 may be implanted in a safe superficial procedure, without penetrating into an abdominal cavity of subject's body 90 and without performing any arterial manipulations in subject's body 90.

One example of an implantation procedure of device 100 in subject's body 90 is described herein with respect to FIG. 5. It is noted that the implantation procedure is not limited to the illustrations in FIG. 5 and to the corresponding description. For example, the implantation procedure need not necessarily include each described step, or in exactly the same order as described. It is also noted that other implantation procedures of device 100 are possible.

A first incision 201 (e.g., 2 cm incision) may be made in subject's body 90 at a groin, above a femoral vein and the femoral vein may be exposed. A second incision 202 (e.g., 1 cm incision) may be made in subject's body 90 at a lower abdomen, above the inguinal ligament. First catheter 110 of device 100 may be tunneled (e.g., subcutaneously) from the lower abdomen to the groin. First catheter 110 may be inserted into the femoral vein (e.g., using a Seldinger technique that includes an insertion of a catheter over a wire) and secured to the femoral vein using first catheter connector 116 (e.g., as described above with respect to FIG. 2C). In some cases, a purse-string stitch (e.g., having a diamond shape) may be made to further secure first catheter 110 catheter to the femoral vein. First catheter 110 may be then washed with blood and first incision 201 above the femoral vein may be closed (e.g., in layers).

A third incision 203 (e.g., 5 cm longitudinal incision) may be made in subject's body 90 at a lateral abdominal wall, and a plane between abdominal wall muscles and transversalis fascia may be dissected. First catheter 110 may be tunneled to the dissected plane and first lumen 112 may be connected to an inlet of pump 120. An outlet of pump 120 may be connected to an inlet of filter 130. An outlet of filter 130 may be connected to second lumen 114 of first catheter 110. Second incision 202 at the lower abdomen may be closed.

A fourth incision 204 (e.g., 2 cm suprapubic incision) in subject's body 90 may be made directly above urinary bladder 94 (e.g., under ultrasound guiding). Second catheter 140 may be inserted to urinary bladder 94, secured to urinary bladder 94 using second catheter connector 142, and tunneled and connected to filter 130 (e.g., to collecting bag 132). Fifth substantially circular incision 205 (e.g., 0.5 cm incision) may be made, for example laterally to third incision 203, for tunneling drivelines (e.g., drivelines 152a/170a/170b described hereinabove) external to subject's body 90. Fourth incision 204 may be closed. Third incision 203 may be closed. Device 100 may be turned on.

The disclosed implantable renal replacement therapy device may provide a continuous renal replacement therapy for a subject while maintaining the subject's ability to perform normal daily activities including normal urination. The device may be implanted in the subject's body between abdominal wall muscles a transversalis fascia membrane in a simple and safe superficial procedure, without penetrating into an abdominal cavity of the subject's body and without performing any arterial manipulations in the subject's body. The superficial procedure may avoid (or at least significantly reduce) abdominal complications associated with intra-abdominal implantations. The superficial implantation may provide safe and minimally invasive access to the implanted device, for example in the case of post-implantation malfunctions and/or complications. Absence of arterial manipulations during implantation of the device may eliminate possible life-threatening arterial complications associated with arterial manipulations procedures. Flexible and flat filter (e.g., thin and flat filter, having a uniform thickness substantially smaller than a width or length of the filter) of the device may significantly reduce the complexity of its implantation and significantly reduce inconvenience and lifestyle limitations that may be caused thereby.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. An implantable renal replacement therapy device, the device comprising:
    a first catheter configured to be inserted into a blood vessel in a subject's body;
    a pump in fluid communication with the first catheter, the pump is configured to pump subject's blood from the blood vessel;
    a filter in fluid communication with the pump, the filter is configured to:
        receive the subject's blood from the pump, and
        filter the received blood to provide a filtered blood and a filtrate liquid,
        wherein the filter is in fluid communication with the first catheter to cause an outflow of the filtered blood from the filter to the blood vessel; and
    a second catheter in fluid communication with the filter and configured to be inserted into an urinary bladder in the subject's body to cause an outflow of the filtrate liquid from the filter to the urinary bladder;
    wherein the first catheter comprises:
        a first lumen in fluid communication with the pump; and
        a second lumen in fluid communication with the filter.

2. The device of claim 1, wherein the first catheter comprises a first catheter connector configured to connect the first catheter to the blood vessel and to prevent motion of the first catheter with respect to the blood vessel.

3. The device of claim 2, wherein the first catheter connector comprises:
    a first inflatable member connected to an outer surface of the first catheter; and
    a second inflatable member connected to the outer surface of the first catheter at a predefined first distance from the first inflatable member and a predefined second distance from a distal sharp end of the first catheter;
    wherein, when inflated, the first and second inflatable members are configured to receive a wall of the blood vessel therebetween to prevent motion of the first catheter with respect to the blood vessel.

4. The device of claim 1, wherein the pump is an axial or centrifugal flow pump.

5. The device of claim 1, wherein the filter has a substantially flat flexible structure.

6. The device of claim 1, wherein the filter comprises:
    a filtrate collecting bag in fluid communication with the second catheter; and
    a filtering membrane positioned within the filtrate collecting bag, the filtering membrane having filtering membrane interior in fluid communication with the pump and configured to receive the subject's blood from the pump.

7. The device of claim 6, wherein the filtering membrane is made of a silicone and comprises a plurality of pores having high permeability for selected liquids and selected electrolytes.

8. The device of claim 6, wherein the filtering membrane has a wavy structure in its cross-section.

9. The device of claim 6, wherein the filter further comprises a second membrane surrounding the filtering membrane, the second membrane having lower permeability for the selected liquids and the selected electrolytes as compared to the permeability of the filtering membrane to cause reabsorption of excess liquids of the selected liquids and excess electrolytes of the selected electrolytes within the filtered blood.

10. The device of claim 1, wherein the filter comprises a conduit for injection of liquids into the filter, wherein the conduit is configured to extend external to the subject's body.

11. The device of claim 1, wherein the second catheter comprises an adjustable ring configured to adjust a diameter of the second catheter based on a desired blood filtration rate and a desired filtrate outflow rate.

12. The device of claim 1, wherein the second catheter comprises a second catheter connector configured to connect the second catheter to the urinary bladder and to prevent motion of the second catheter with respect to the urinary bladder.

13. The device of claim 12, wherein the second catheter connector comprises:
    a first inflatable member connected to an outer surface of the second catheter; and
    a second inflatable member connected to the outer surface of the second catheter at a predefined first distance from the first inflatable member and a predefined second distance from a distal sharp end of the second catheter;
    wherein, when inflated, the first and second inflatable members are configured to receive a wall of the urinary bladder therebetween to prevent motion of the second catheter with respect to the urinary bladder.

14. The device of claim 1, further comprising a power source configured to be implanted in the subject's body to provide power to the pump.

15. The device of claim 14, wherein the power source is chargeable.

16. The device of claim 1, further comprising an external non-implantable power source to at least one of: (i) provide power to the pump, and (ii) charge a power source that provides power to the pump.

17. The device of claim 1, further comprising one or more sensors configured to be implanted in the subject's body and measure one or more properties of at least one of the subject's blood and subject's blood filtration work products.

18. The device of claim 17, further comprising a controller configured to:
- receive the one or more measured properties from the one or more sensors; and
- control a pump rate or speed of the pump based on the one or more measured properties and a desired filtration rate of the subject's blood.

19. The device of claim 17, wherein the controller is configured to generate one or more notifications based on the one or more measured properties.

* * * * *